(12) United States Patent
Kroll et al.

(10) Patent No.: US 7,587,239 B1
(45) Date of Patent: Sep. 8, 2009

(54) CARDIAC PACEMAKER SYSTEM, LEAD AND METHOD FOR REJECTING FAR-FIELD SIGNALS

(75) Inventors: Mark W. Kroll, Crystal Bay, MN (US); John W. Poore, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 676 days.

(21) Appl. No.: 11/475,482

(22) Filed: Jun. 26, 2006

Related U.S. Application Data

(63) Continuation of application No. 10/671,367, filed on Sep. 24, 2003, now abandoned.

(51) Int. Cl.
 *A61N 1/362* (2006.01)
(52) U.S. Cl. .............. 607/9; 600/509; 128/902
(58) Field of Classification Search ........... None
 See application file for complete search history.

(56) References Cited

U.S. PATENT DOCUMENTS

| | | | | |
|---|---|---|---|---|
| 4,289,134 A | 9/1981 | Bernstein | ............ | 128/419 PG |
| 4,365,639 A | 12/1982 | Goldreyer | ............ | 128/786 |
| 4,444,195 A | 4/1984 | Gold | ............ | 128/642 |
| 4,513,752 A | 4/1985 | Weyant | ............ | 128/696 |
| 4,535,776 A * | 8/1985 | Strandberg et al. | ............ | 607/9 |
| 4,579,119 A | 4/1986 | Callaghan | ............ | 128/419 PG |
| 4,825,870 A | 5/1989 | Mann et al. | ............ | 128/419 PG |
| 4,848,352 A | 7/1989 | Pohndorf et al. | ............ | 128/642 |
| 4,892,102 A | 1/1990 | Astrinsky | ............ | 128/642 |
| 5,127,403 A | 7/1992 | Brownlee | ............ | 128/419 P |
| 5,265,623 A | 11/1993 | Kroll et al. | ............ | 607/122 |
| 5,385,146 A | 1/1995 | Goldreyer | ............ | 128/642 |
| 5,405,375 A | 4/1995 | Ayers et al. | ............ | 607/122 |
| 6,278,894 B1 | 8/2001 | Salo et al. | ............ | 600/547 |
| 6,341,234 B1 | 1/2002 | Thong et al. | ............ | 607/9 |
| 6,434,428 B1 | 8/2002 | Sloman et al. | ............ | 607/28 |
| 6,456,881 B1 | 9/2002 | Bornzin et al. | ............ | 607/27 |
| 6,496,730 B1 | 12/2002 | Kleckner et al. | ............ | 607/9 |
| 6,553,259 B2 | 4/2003 | Mouchawar et al. | ............ | 607/11 |
| 2002/0002389 A1 | 1/2002 | Bradley et al. | ............ | 607/8 |
| 2002/0123784 A1 | 9/2002 | Westendorp | ............ | 607/122 |

* cited by examiner

*Primary Examiner*—Kennedy J Schaetzle

(57) ABSTRACT

An implantable cardiac lead comprises a lead body having a proximal end and a distal end, the proximal end of the lead body carrying a connector assembly connectable to an implantable medical device, and the distal end of the lead body carrying a distal electrode, a proximal electrode and an intermediate electrode positioned between the distal and proximal electrodes. The distal and proximal electrodes are connected together at a node point located within the distal end of the lead body, the node point being electrically connected to a first terminal contact on the connector assembly and the intermediate electrode being electrically connected to a second terminal contact on the connector assembly. Preferably, the intermediate electrode is positioned approximately midway between the distal and proximal electrodes. Also disclosed are a system and a method for differentiating signals generated by a plurality of electrodes carried by a lead body to provide an output signal representative of a second spatial derivative of the generated signals, the output signal being substantially devoid of far-field signals.

6 Claims, 5 Drawing Sheets

CARDIAC PACEMAKER SYSTEM, LEAD AND METHOD FOR REJECTING FAR-FIELD SIGNALS

CROSS-REFERENCE TO RELATED APPLICATIONS

This application is a continuation of U.S. patent application Ser. No. 10/671,367, filed Sep. 24, 2003, now abandoned.

FIELD OF THE INVENTION

The present invention relates generally to cardiac pacing and sensing, and more particularly to cardiac pacing and sensing systems, leads and methods for rejecting or canceling sensed far-field signals.

BACKGROUND OF THE INVENTION

Cardiac pacemaker lead systems fulfill two functions. The first function is to provide an electrical conduit by which a pacemaker output pulse is delivered to stimulate the local tissue adjacent to the distal tip of the lead. The second function is to sense local, intrinsic cardiac electrical activity that takes place adjacent to the distal tip of the lead.

The advantages of providing pacing therapies to both the right and left heart chambers are well established. For example, in four chamber pacing systems, four pacing leads, typically bipolar leads, are positioned for both pacing and sensing of the respective heart chambers. To provide right side pacing and sensing, leads are implanted directly in the right atrium and/or right ventricle. To provide left side stimulation and sensing, leads are transvenously implanted in the coronary sinus region, for example, in a vein such as the great vein, the left posterior ventricular (LPV) vein, or other coronary veins, proximate the left ventricle of the heart. Such placement avoids the risks associated with implanting a lead directly within the left ventricle which can increase the potential for the formation of blood clots which may become dislodged and then carried to the brain where even a small embolism could cause a stroke. (As used herein, the phrase "coronary sinus region" refers to the coronary sinus, great cardiac vein, left marginal vein, left posterior ventricular vein, middle cardiac vein, and/or small cardiac vein or any other coronary vein accessible by way of the coronary sinus.)

One of the problems with cardiac pacing and sensing systems is their inability to suppress far-field electrical signals. These signals are generated by depolarizations of body tissue in areas remote from the local sensing site and are manifested as propagated voltage potential wavefronts carried to and incident upon the local sensing site. A far-field signal may comprise the intrinsic signal originating from the chamber of the heart opposite the one in which a lead electrode is located. For example, for a lead electrode implanted in the right atrium, the ventricular R-wave comprises a far-field signal whose amplitude can easily swamp the smaller P-wave signal sought to be sensed thereby making difficult the discrimination of a P-wave from the higher energy QRS complex (sometimes referred to as the R-wave).

Sensing in the coronary sinus also presents far-field signal issues. For example, deep in the coronary sinus where sensing of left ventricle activation would be expected, the right atrium signal may be sensed as a far-field signal. Similarly, in the proximal coronary sinus, where the sensing of left atrial activations would be expected, far-field signals originating in the left ventricle may be extremely strong. Moreover, early right ventricular activation can interfere with sensing of left ventricle signals.

The sensing electrode(s) detect or sense the voltages of these far-field signals and interpret them as depolarization events taking place in the local tissue when such polarizations are above the threshold sensing voltage of the system. When far-field signal voltages greater than the threshold voltage are applied to the sensed signal processing circuitry of the pulse generator or pacemaker, activation of certain pacing schemes or therapies can be erroneously triggered.

With the development of programmable, universal stimulation/sensing systems, that is, three and four chamber combination pacemaker-cardioverter-defibrillators, accurate sensing of cardiac signals has become even more critical, and the management, suppression and/or elimination of far-field signals is vitally important to allow appropriate device algorithms to function without being confused by the undesirable far-field signals.

Approaches to the problem of far-field signal sensing include configuring the circuitry of the pacemaker to attenuate far-field signals, introducing a blanking period long enough to prevent the sensing of unwanted signals, and providing timing and logic circuitry to detect "crosstalk" between paced chambers of the heart and to provide compensation in the event "crosstalk" is detected. These solutions are described in U.S. Pat. Nos. 4,513,752 and 4,825,870 assigned to the owner of the present invention.

U.S. Pat. No. 4,579,119 discloses a tripolar atrial pacing and sensing lead comprising a tip electrode and a pair of spaced-apart ring electrodes. The distal ring electrode, that is, the ring electrode positioned intermediate the tip electrode and the more proximal of the pair of ring electrodes, is at all times connected to one of the two input terminals of a sense amplifier. A multiplexer at the proximal end of the lead selectively connects the remaining electrodes to a pulse generator and to the sense amplifier. Thus, during pacing the tip electrode and the proximal ring electrode are connected to the pulse generator. During sensing, the multiplexer connects the parallel combination of the tip electrode and the proximal ring electrode to the other sense amplifier input. The placement of this tripolar lead in the right atrium is said to reduce both cross-sensing, that is, the sensing of far-field signals originating in the ventricle, and polarization potentials which would otherwise mask the evoked response. The '119 patent, however, requires an electrical conductor extending the entire length of the lead body for each of the electrodes. In addition, the '119 patent does not deal with left heart pacing and sensing.

U.S. Patent Application Publication US2002/0123784A1 discloses a tripolar pacing and sensing lead including three electrodes separated by interelectrode spacings that are said to maximize both sensing and pacing activities. The electrode pair comprising the tip and first ring electrodes provides local sensing capabilities within either the atrium or the ventricle, while the electrode pair comprising the tip and second ring electrodes provides pacing capabilities. Far-field artifacts are said to be virtually eliminated by minimizing the distance between the two sensing electrodes. Like U.S. Pat. No. 4,579,119, the tripolar electrode arrangement of publication US2002/0123784A1 requires a separate electrical conductor running the length of the lead for each electrode and the publication does not address left heart pacing and sensing.

SUMMARY OF THE INVENTION

In accordance with one specific, exemplary embodiment of the present invention there is provided an implantable cardiac lead for transmitting electrical signals between an implantable medical device and selected body tissue in the heart and for rejecting sensed far-field signals. The lead comprises a lead body having a proximal end and a distal end, the proximal end of the lead body carrying a connector assembly connectable to the implantable medical device, and the distal end carrying a plurality of spaced-apart electrodes. The plurality of electrodes may comprise a distal electrode, a proximal electrode and an intermediate electrode positioned between the distal and proximal electrodes. The distal and proximal electrodes are connected together at a node point located within the distal end of the lead body, the node point of the distal and proximal electrodes being electrically connected to a first terminal contact on the connector assembly and the intermediate electrode being electrically connected to a second terminal contact on the connector assembly. Pursuant to an aspect of the invention, the intermediate electrode is positioned approximately midway between the distal and proximal electrodes.

In accordance with another, specific exemplary embodiment of the present invention, there is provided an implantable stimulation lead for transmitting electrical signals between an implantable medical device and selected body tissue in the heart and for rejecting sensed far-field signals, wherein the lead comprises a lead body having a proximal end and a distal end, the proximal end of the lead body carrying a connector assembly connectable to the implantable medical device, and the distal end carrying at least three spaced-apart electrodes comprising a distal electrode, a proximal electrode and an intermediate electrode positioned between the distal and proximal electrodes. A first electrical conductor enclosed within the lead body electrically couples the parallel combination of the distal and proximal electrodes with a first terminal contact on the connector assembly, and a second electrical conductor enclosed within said lead body electrically couples the intermediate electrode with a second terminal contact on the connector assembly. Preferably, the intermediate electrode is positioned approximately midway between the distal and proximal electrodes, and further, the distal and proximal electrodes are electrically connected together at a node point located within the distal end of the lead body, the first electrical conductor connecting said node point with said first terminal contact on the connector assembly.

Pursuant to yet another specific, exemplary embodiment of the invention, there is provided an implantable cardiac pacing and sensing system that substantially completely rejects sensed far-field signals. The system comprises a lead for transmitting electrical signals between an implantable medical device and selected body tissue in the heart, the lead comprising a lead body having a proximal end and a distal end, the proximal end of the lead body carrying a connector assembly connectable to the implantable medical device and the distal end of the lead body carrying a plurality of electrodes spaced apart along an electrode axis. The plurality of electrodes includes a distal electrode, a proximal electrode and an intermediate electrode disposed between the distal and proximal electrodes, the electrodes being disposed to sense electrical signals, including far-field signals, propagated by the tissue of the heart. The sensed signals have a second spatial derivative, $d^2v/dx^2$, where v is the amplitude of the voltage of the sensed signals and x is the distance along said electrode axis, and wherein the second spatial derivative of the sensed far-field signals is substantially zero. The system further comprises a signal processing circuit contained within the implantable medical device, the circuit being responsive to the sensed signals generated by the electrodes to provide an output signal representing the second spatial derivative of the sensed signals, whereby said output signal is substantially devoid of far-field signals. Pursuant to another aspect of this embodiment, the output signal of the signal processing circuit represents the difference between the magnitudes of a first signal and a second signal, the first signal representing the difference between the magnitudes of the signals generated by the distal and intermediate electrodes and the second signal representing the difference between the magnitudes of the signals generated by the intermediate and proximal electrodes.

In accordance with the invention there is also provided a method of rejecting sensed far-field signals incident upon the electrodes of a cardiac pacemaker lead having a distal end carrying a plurality of spaced-apart electrodes including a distal electrode, a proximal electrode and an intermediate electrode positioned between the distal and the proximal electrodes. The electrodes generate signals including the far-field signals. The method comprises the steps of generating a first signal representing the difference between the magnitudes of the signals generated by the distal and intermediate electrodes, generating a second signal representing the difference between the magnitudes of the signals generated by the intermediate and proximal electrodes, and generating a third signal representing the difference between the first and second signals, the third signal being substantially devoid of the far-field signals.

BRIEF DESCRIPTION OF THE DRAWINGS

The foregoing and other objects, features and advantages of the invention will be evident to those skilled in the art from the detailed description below, taken together with the accompanying drawings, in which.

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators are used to refer to like parts or elements throughout. Moreover, the context in which the invention is principally shown and described herein, namely, a cardiac stimulation and sensing system using a single lead intended for placement in the coronary sinus region of the heart for left heart stimulation and sensing, is illustrative only; it will be understood by those skilled in the art that the invention is equally applicable to right heart stimulation and sensing systems as well as multi-chamber, multi-lead systems.

Figure 1:
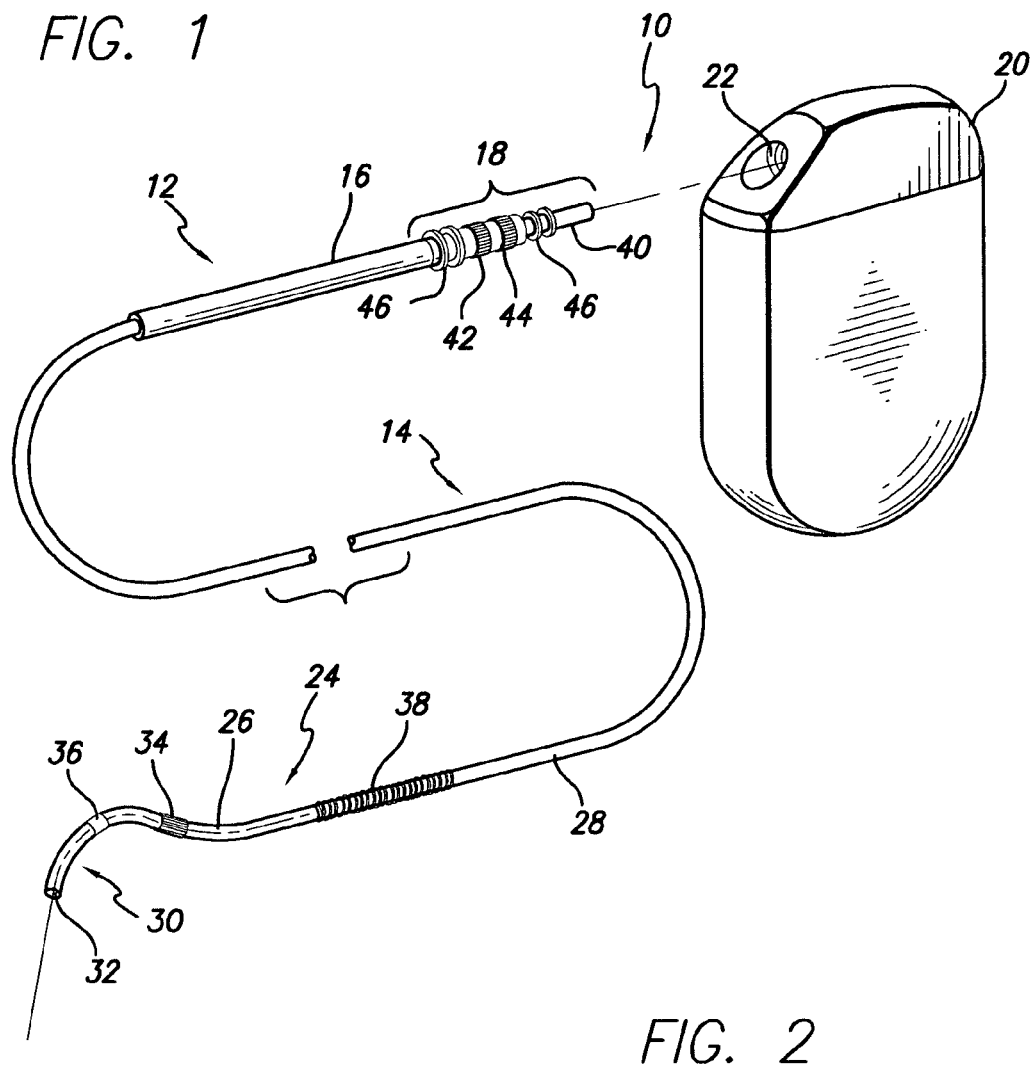
FIG. 1 is a perspective, exploded view of an implantable, far-field rejecting cardiac pacing and sensing system in accordance with one embodiment of the invention, the system including a transvenous lead carrying a plurality of electrodes for placement in the coronary sinus region of the heart.
Figure 2:
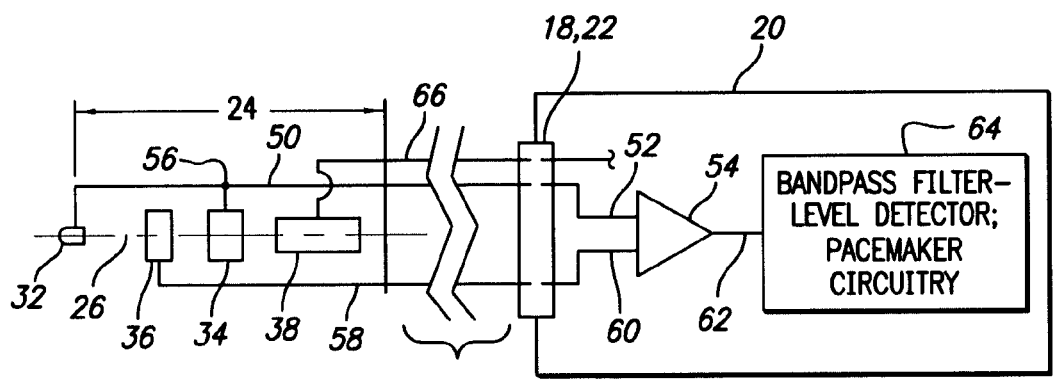
FIG. 2 is a circuit schematic showing the manner in which the electrodes carried by the lead of FIG. 1 may be electrically connected to reject far-field signals.

With reference to FIGS. 1 and 2, there is shown a cardiac stimulation and sensing system 10 in accordance with one preferred embodiment of the present invention. The system 10 comprises an implantable transvenous lead 12 comprising a lead body 14 having a proximal end 16 carrying a connector assembly 18 for electrically connecting the lead 12 to an implantable medical device 20 having a receptacle 22 for receiving the connector assembly. The implantable medical device 20 may comprise a pacemaker or a pacemaker combined with cardioverting and/or defibrillating functions. The lead body 14 further comprises a distal end 24 carrying a plurality of electrodes lying along a longitudinal electrode axis 26 and adapted to be placed within the coronary sinus region of the heart. The lead body 14 is covered by a tubular sheath or housing 28 made of an insulating, biocompatible, biostable material such as silicone rubber or polyurethane.

In the specific embodiment under consideration, the distal end 24 of the lead body 14 preferably has a length corresponding to the coronary sinus and its associated coronary vessels overlying the left side of the heart, ranging from approximately 4 cm to approximately 20 cm and preferably from about 6 cm to about 10 cm. By further way of example and not limitation, the lead body 14 may be isodiametric with an outside diameter of the distal end of the lead body may range from about 0.026 inch (2F) to about 0.091 inch (7F). In accordance with well known techniques, the lead body 14 may have a lubricious coating to facilitate its movement through a left heart delivery introducer and the patient's vascular system.

The distal end 24 of the lead body 14 is preferably configured to stabilize the distal end within a target coronary vessel of the coronary sinus region. More specifically, the distal end 24 of the lead body 14 may include passive fixation or anchoring means 30 comprising, for example, one or more preformed projections, humps, helices, spirals, S-shaped bends or other structural elements or features manufactured into the distal end 24 of the lead body 14 designed to provide biased contact between the distal end of the lead body and the inner wall of the target vessel so as to create frictional forces sufficient to wedge or stabilize the distal end and prevent its displacement or dislodgement. The passive fixation means 30 may also include texturization of at least a portion of the distal end 24 of the lead body to promote rapid blood clotting and resulting fibrotic growth to further help stabilize or anchor the distal end of the lead body. Still further, the fixation means may alternatively or in addition comprise a fixation mechanism such as a screw-in helix (not shown) which, in one form thereof, may be electrically active to serve as a tip electrode. The helix may be fixed relative to the distal end 24 of the lead body 14 or may be an extendable/retractable element in accordance with expedients well known in the art.

The tip electrode of a lead implanted in the coronary sinus region can pace and sense left side ventricular activity. When such a lead includes a second electrode proximal of the tip electrode and residing in the coronary sinus above the left ventricle closely adjacent to the left atrium of the heart, pacing and sensing of left atrial activity is made possible. Moreover, the lead may include one or more electrodes for the delivery of electrical shocks for terminating tachycardia and/or fibrillation. Such cardioverting/defibrillating electrodes may be used by themselves or may be combined with pacing and/or sensing electrodes.

Pursuant to the first embodiment, the plurality of electrodes carried by the distal end 24 of the lead body may comprise, respectively, a distal or tip electrode 32, a proximal electrode 34 in the form of a ring electrode and an intermediate electrode 36 also in the form of a ring electrode positioned between the distal and proximal electrodes 32 and 34. Preferably, the electrode 36 is positioned approximately midway between the distal and proximal electrodes 32 and 34. In conventional fashion, the electrodes may be formed of MP35N, MP35N/Ag, iridium, platinum, titanium nitride, or a conductive polymer. The ring electrodes 34 and 36 may have any lengths compatible with maintaining the flexibility of the distal end of the lead body. The interelectrode spacings between the electrodes are preferably such as to be compatible with or to optimize the pacing and sensing of the left atrium and ventricle. The determination of such spacings will typically depend upon such factors as the particular coronary vessel selected to receive the distal end of the lead, the patient's anatomy, and so forth. Generally, it is desirable to have the interelectrode spacings sufficiently small to allow the tip and ring electrodes to be placed in a target coronary vessel such as the left posterior ventricle vein. Such placement of the electrodes tends to ensure achieving electrical capture of the left ventricle. ("Electrical capture" is defined as the successful depolarization and contraction of a cardiac chamber, that is, atrium or ventricle, in response to an electrical stimulation pulse generated by an implantable medical device such as a pacemaker or an implantable cardioverter/defibrillator (ICD).)

The distal end 24 of the lead body 14 may also carry a cardioverting/defibrillating shocking electrode 38 proximal of the proximal ring electrode 34. The shocking electrode 38 may comprise a conventional, elongated electrically conductive coil wound around the outside surface of the lead body housing or, for greater flexibility, may comprise a series of spaced-apart, relatively short rings of metal or a conductive polymer.

As noted, the connector assembly 18 carried by the proximal end 16 of the lead body 14 is adapted to electrically and mechanically couple the lead body to the implantable medical device 20 via the receptacle 22 which contains terminals connected to electronic circuitry enclosed within the medical device. For the embodiment under consideration, the connector assembly 18 includes a tubular contact pin 40 and two ring terminal contacts 42 and 44 spaced apart along the body of the connector assembly. Each of the pin and ring contacts 40, 42 and 44 is positioned to engage a corresponding electrical terminal within the receptacle 22. To prevent ingress of body fluids into the receptacle, the connector assembly 18 may be provided with spaced-apart sets of seals 46. Also as known in the art, the connector assembly 18 may comprise a bifurcated or trifurcated structure, each leg of which is received by a corresponding receptacle in an implantable medical device. Further, in accordance with well known implantation techniques, a stylet or guide wire for delivering and steering the distal end of the lead body during placement thereof within a coronary vessel is inserted through the contact connector pin 40 and into a longitudinal passageway within the lead body housing 28, which passageway may comprise the lumen of a coil dedicated for that purpose or also serving as an electrical conductor connecting the contact pin 40 with the tip electrode 32. Further, where the tip electrode comprises a helical, screw-in electrode, the electrical conductor may also function as an actuator for extending and retracting the helical electrode.

The insulating, tubular housing 28 encloses a plurality of electrical conductors of MP35N or MP35N/Ag alloy or the like connecting the electrodes along the distal end of the lead body with the terminal contacts on the connector assembly carried by the proximal end of the lead body. Preferably, the housing 28 comprises a multilumen structure and the conductors comprise multifilar, braided cables although, as suggested earlier, one or more coil conductors in combination with cable conductors may also be used. The use of coil conductors, particularly within the distal end of the lead body, provides greater lead body flexibility facilitating its maneuvering around sharp bends and corners in the coronary venous vasculature.

With reference specifically to FIG. 2, there is shown schematically one preferred embodiment of the electrical connections of the electrodes with the electronic circuitry contained in the implantable medical device 20. The parallel combination of the tip electrode 32 and the proximal ring electrode 34 is connected by a first electrical conductor 50, via a terminal contact on the connector assembly 18 and an associated terminal within the receptacle 22, to an input 52 of a differential amplifier 54. Preferably, the tip and proximal ring electrodes 32 and 34 are connected at a node point 56 within the distal end 24 of the lead body. Accordingly, only a single electrical conductor 50 running the length of the lead body is needed to connect the combination of the tip and proximal ring electrodes 52 with the amplifier input 52. The intermediate ring electrode 36 is connected by a second electrical conductor 58 via the connector assembly and receptacle 18, 22 to the other input 60 of the differential amplifier 54. The output 62 of the differential amplifier 54 is connected to appropriate, conventional bandpass filter, level detector and related pacemaker circuitry 64. The shocking electrode 38 is connected via an electrical conductor 66, the connector assembly 18 and the receptacle 22 to cardioverting/defibrillating control, charging and output circuits (not shown) within the implantable medical device 20.

The electrodes 32, 34 and 36 sense local voltage signals of interest as well as unwanted far-field voltage signals sought to be cancelled or rejected. Far-field voltages detected at the sensing site tend to satisfy: v=f(x), where f(x) is a substantially linear function, v is the sensed far-field voltage and x is distance in the direction of the electrode axis 26. As a consequence, the far-field signal voltage appearing at the node point 56 approximates the average of the far-field signal voltages detected by the parallel-connected tip and proximal ring electrodes 32 and 34. Thus, the difference between the far-field signal voltage at the node point 56 and the far-field signal voltage sensed by the intermediate electrode 36 (which difference is seen at the differential amplifier output) is approximately zero.

It will be seen that the sensing system of the first embodiment of the invention does not require any additional amplifiers, over and above those used in conventional bipolar sensing, so that a total of only three electrical conductors 50, 58 and 66 (two for the tip and ring electrodes and one for the shocking coil) are needed.

Figure 3:
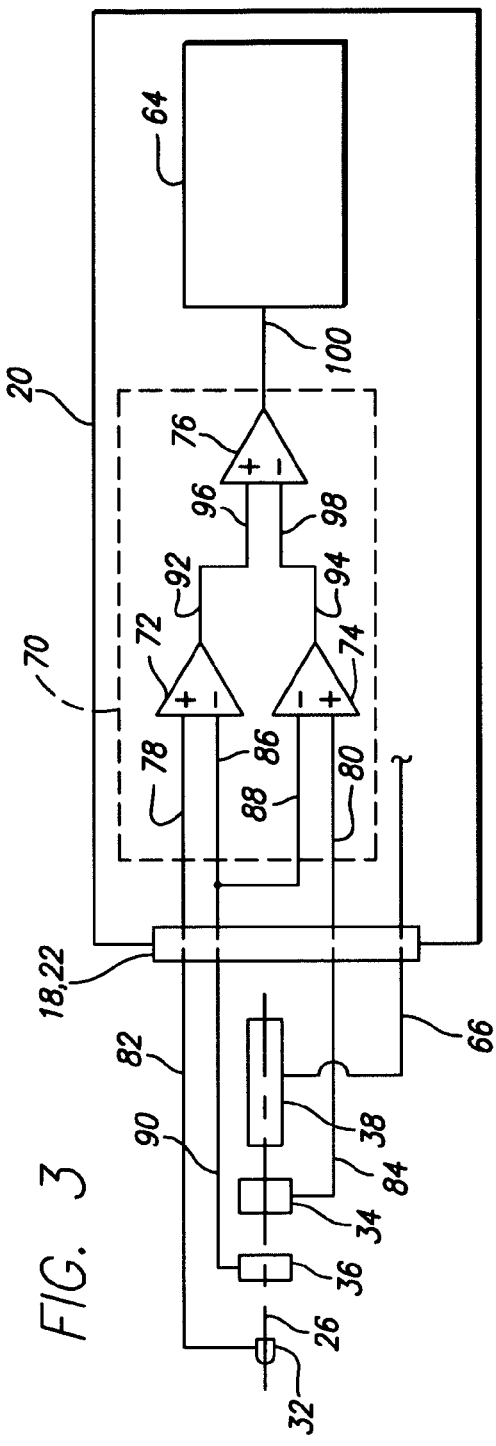
FIG. 3 is a circuit schematic showing the manner in which the electrodes carried by the lead in FIG. 1 may be electrically connected to reject far-field signals in accordance with an alternative embodiment of the invention.

FIG. 3 shows a circuit diagram of an alternative embodiment of the invention that, although requiring two additional differential amplifiers and an additional conductor, provides higher performance than the first embodiment. The performance gain is achieved by using a signal processing circuit 70 comprising three differential amplifiers 72, 74 and 76 for second derivative sensing. Instead of simply shorting the distal or tip electrode and the second ring electrode together at a node point within the distal end of the lead, this embodiment provides for the connection of the tip and proximal ring electrodes 32 and 34 to the noninverting inputs 78 and 80, respectively, of the pair of differential amplifiers 72 and 74 by means of electrical conductors 82 and 84. The intermediate electrode 36 is connected to each of the inverting inputs 86 and 88 of the amplifiers 72 and 74 via an electrical conductor 90. The outputs 92 and 94 of the amplifiers 72 and 74 are connected, respectively, to the noninverting input 96 and inverting input 98 of the third differential amplifier 76. As noted, preferably the intermediate ring electrode 36 is approximately centered between the tip and proximal electrodes 32 and 34, respectively. It will be seen that this arrangement provides at the output 100 of amplifier 76 the second spatial derivative, $d^2v/dx^2$, of signals appearing on the inputs of the first and second amplifiers 72 and 74. In the case of far-field signals whose second derivative at a local sensing site is essentially zero, such far-field signals will for all practical purposes not appear at the output of the amplifier immunizing the system from such interfering signals. As before, the output 100 of the amplifier 76 is connected to conventional pacemaker circuitry 64.

Figure 4:
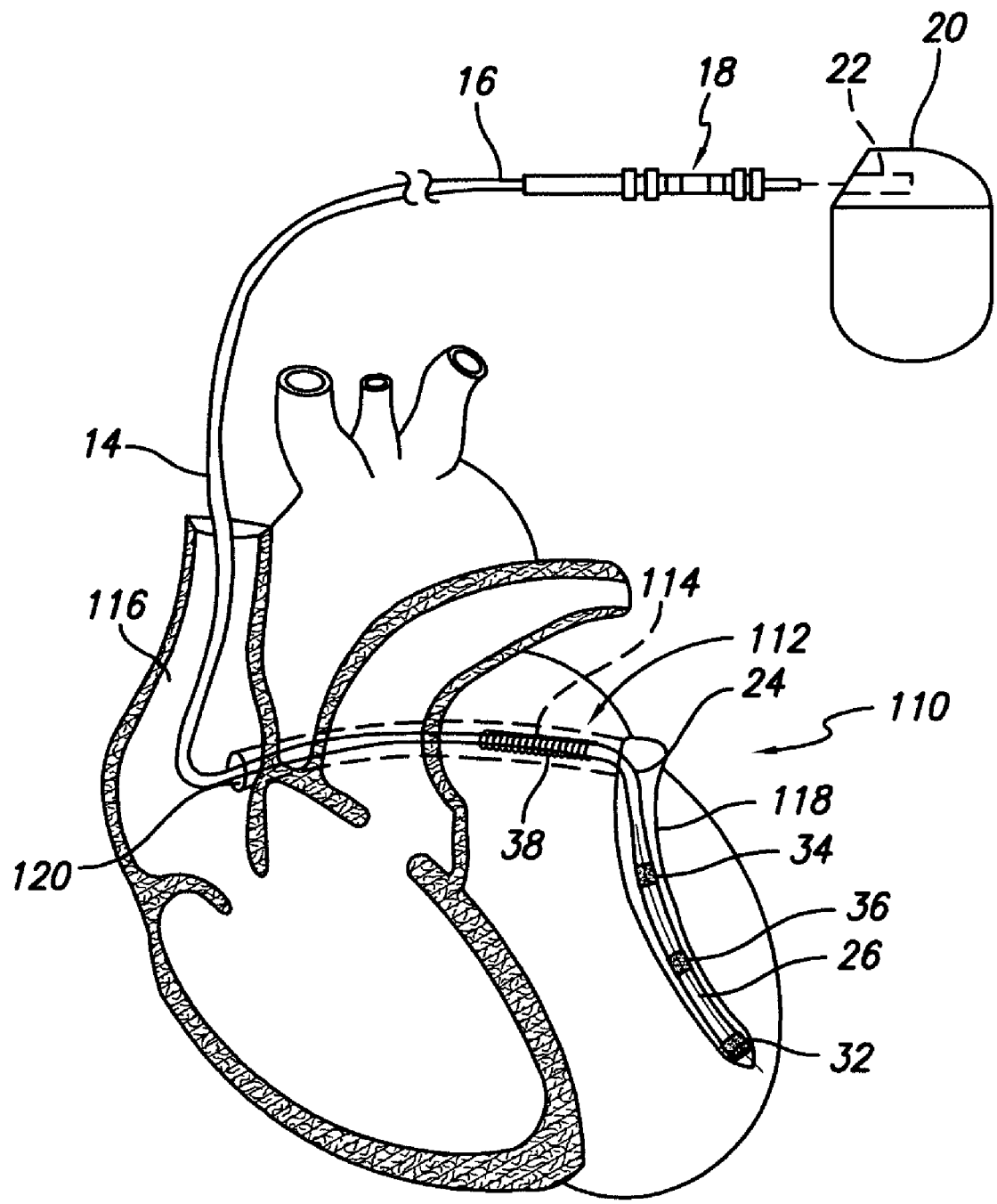
FIG. 4 is a perspective view of the anterior portion of a heart showing the distal end of the implantable lead of FIG. 1 placed within the coronary sinus region of the heart.

FIG. 4 is a perspective view of the anterior portion of the heart 110 showing portions of the relevant anatomy of the coronary sinus region 112. As shown in FIG. 4, the coronary sinus 114 is the main collecting vein of the heart which drains into the right atrium 116. The coronary sinus 114 connects to the left posterior ventricular (LPV) vein 118 and drains into the right atrium 116 through an ostium or coronary os 120.

In one approach to the delivery of the distal end 24 of the lead body 14 to the coronary sinus and/or coronary veins, a "left heart lead delivery" work station or lead introducer adapted to reach into the coronary sinus 114 is used to deliver the lead body into the coronary sinus. The distal portion of the introducer may be curved, with either a single or a compound curve, to allow for ease in advancing the introducer past the coronary os 120 and into the coronary sinus 114. The inserted introducer provides a conduit facilitating and supporting the placement of the lead in the coronary sinus and ultimately into the more distal cardiac veins within the coronary sinus region.

FIG. 4 shows the lead body 14 of the embodiments of FIGS. 1-3 implanted in the coronary sinus region 112 with the tip electrode 32 well within the remote reaches or distal extremity of the LPV vein 118 and the ring electrodes 34 and 36 within the proximal portion of the LPV vein 118. In accordance with the invention, extraneous far-field signals originating, for example, in the right atrium, will be effectively cancelled or rejected.

Figure 5:
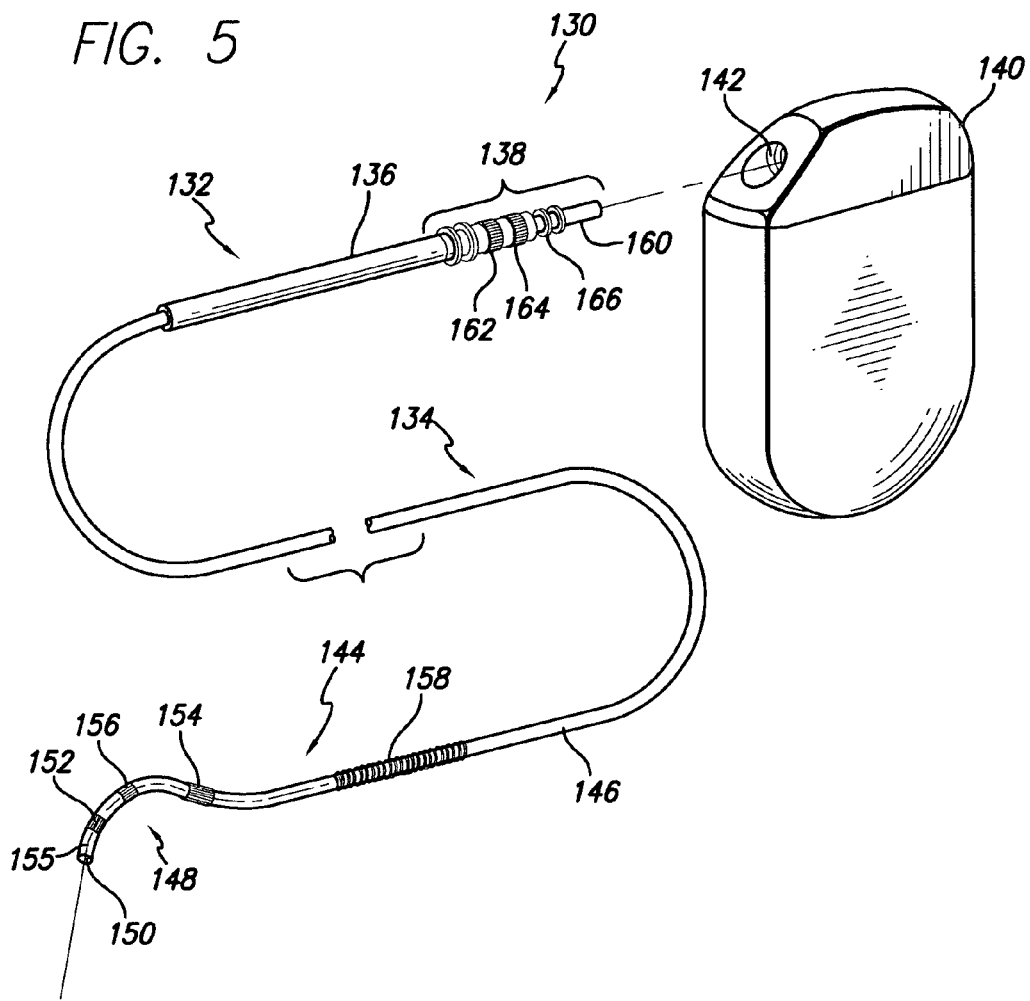
FIG. 5 is a perspective, exploded view of an implantable, far-field rejecting cardiac pacing and sensing system in accordance with another embodiment of the invention, the system including a transvenous lead carrying a plurality of electrodes for placement in the coronary sinus region of the heart.

FIG. 5 shows a far-field rejecting, cardiac stimulation and sensing system 130 in accordance with yet another embodiment of the present invention.

The system 130 comprises a transvenous lead 132 including a lead body 134 having a proximal end 136 carrying a connector assembly 138 for electrically connecting the lead to an implantable medical device 140 such as a pacemaker combined with cardioverting/defibrillating functions. The device 140 has a receptacle 142 for receiving the connector assembly 138. The lead body 134 has a distal end 144 carrying a plurality of cardiac tissue stimulation and/or sensing electrodes disposed along a longitudinal electrode axis 155 and adapted to be placed within the coronary sinus region of the heart. The lead body 134 is covered by a tubular sheath or housing 146 made of an insulating, biocompatible, biostable material such as silicone rubber or polyurethane.

As already described, the distal end 144 of the lead body 134 preferably has a length corresponding to the coronary sinus and its associated coronary vessels overlying the left side of the heart. Also, as already described, the distal end 144 of the lead body may include passive fixation or anchoring means 148 such as a preformed S-shape to help stabilize the distal end within a target coronary vessel of the coronary sinus region.

The plurality of electrodes carried by the distal end 144 of the lead body may comprise, respectively, a tip electrode 150, a first or distal ring electrode 152 proximal of the tip electrode 150 and closest thereto, a second or proximal ring electrode 154 furthest from the tip electrode, and a third or intermediate ring electrode 156 positioned between the first and second ring electrodes 152 and 154. The ring electrodes 152, 154 and 156 may have any lengths compatible with maintaining the flexibility of the distal end of the lead body. The interelectrode spacings between the electrodes are preferably such as to be compatible with or to optimize the pacing and sensing of the left atrium and ventricle. The determination of such spacings will typically depend upon such factors as the particular coronary vessel selected to receive the distal end of the lead, the patient's anatomy, and so forth. Generally, to ensure capture of the left ventricle, it is desirable to have the interelectrode spacings sufficiently small to allow the tip electrode 150 and at least the two ring electrodes 152 and 156 to be placed in a target coronary vessel such as the left posterior ventricle vein. However, for optimum performance, the preferred spacing between the ring electrodes 152 and 156 is approximately equal to the spacing between the ring electrodes 154 and 156, that is, the ring electrode 156 is approximately centered between the electrodes 152 and 154.

The distal end 144 of the lead body may also carry a cardioverting/defibrillating shocking electrode 158 proximal of the proximal ring electrode 154.

The connector assembly 138 includes a tubular contact pin 160 and three terminal contacts 162, 164 and 166 spaced apart along the body of the connector assembly. Each of the pin and ring terminal contacts 160, 162, 164 and 166 is positioned to engage a corresponding electrical terminal within the receptacle 142 in the implantable medical device 140.

The insulating, tubular housing 146 encloses a plurality of electrical conductors of MP35N or MP35N/Ag alloy or the like connecting the electrodes along the distal end of the lead body with corresponding ones of the terminal contacts on the connector assembly 138. Preferably, as before, the housing 146 comprises a multilumen structure and the conductors preferably comprise multifilar, braided cables although, as suggested earlier, one or more coil conductors in combination with cable conductors may also be used.

Figure 6:
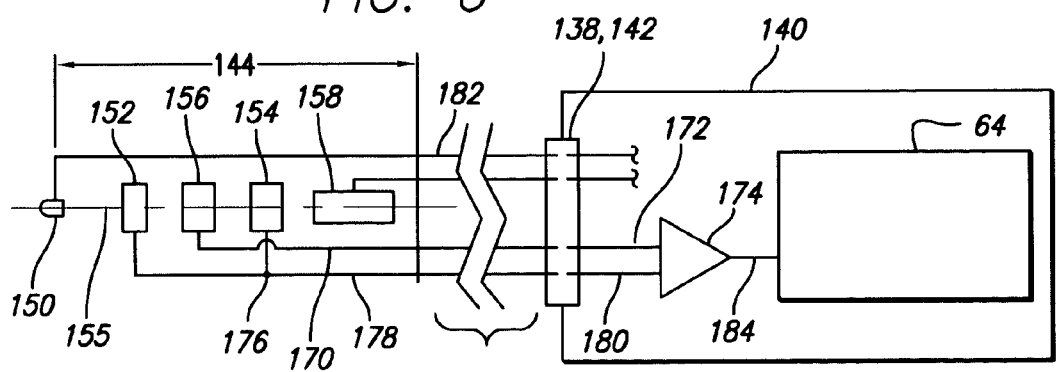
FIG. 6 is a circuit schematic showing the manner in which the electrodes carried by the lead of FIG. 5 may be electrically connected to reject far-field signals.

With reference now to FIG. 6, there is shown schematically one form of the electrical connections of the various electrodes with the electronic circuitry 64 contained in the implantable medical device 140. The circuit of FIG. 6 is similar to that shown in FIG. 2. The intermediate ring electrode 156 is connected by an electrical conductor 170 via the connector assembly 138 and receptacle 142 to an input 172 of a differential amplifier 174. The distal and proximal ring electrodes 152 and 154 are electrically connected together at a node point 176 preferably located within the distal end 144 of the lead body; the node point 176 is connected, via a single electrical conductor 178, the connector assembly 138 and the receptacle 142, to another input 180 of the amplifier 174. The tip electrode 150, used only for pacing, is connected to the pacemaker circuitry by means of an electrical conductor 182.

The shocking electrode 158 is connected via the connector assembly 138 and associated receptacle 142, to cardioverting/defibrillating control, charging and output circuits (not shown) within the implantable medical device 140. For reasons explained in connection with the embodiment of FIG. 2, the signal at the output 184 of the amplifier 174 will essentially be free of far-field components.

It will be seen that the sensing system of this embodiment of the invention does not require any additional amplifiers, over and above those used in conventional bipolar sensing, so that a total of only four conductors (three for the tip and ring electrodes 150, 152, 154 and 156 and one for the shocking coil 158) are needed. In this way, the lead 130 allows use of the IS-4 connector standard.

Figure 7:
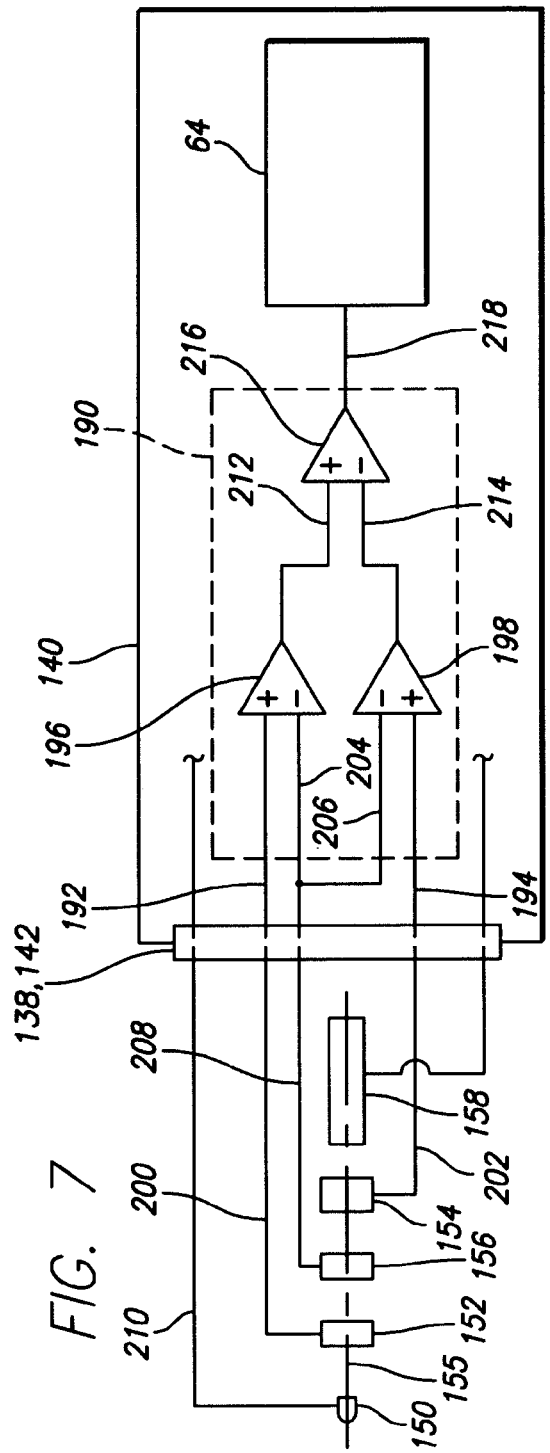
FIG. 7 is a schematic diagram showing the manner in which the electrodes carried by the lead of FIG. 5 may be electrically connected to reject far-field signals in accordance with yet another embodiment of the invention.

FIG. 7 shows a circuit schematic of an alternative embodiment of the invention similar to that of FIG. 3 providing a performance gain achieved by using a signal processing circuit 190 of the kind described in connection with FIG. 3 for second derivative sensing. Again, instead of simply shorting the distal and proximal ring electrodes at a node point, this embodiment provides for the connection of the distal and proximal ring electrodes 152 and 154 to the noninverting inputs 192 and 194, respectively, of a pair of differential amplifiers 196 and 198 by means of electrical conductors 200 and 202. The intermediate ring electrode 156 is connected to both of the inverting inputs 204 and 206 of the amplifiers 196 and 198 via an electrical conductor 208. The tip electrode 150, used only for pacing, is connected to appropriate pacemaker circuitry via an electrical conductor 210. The outputs of the differential amplifiers 196 and 198 are connected, respectively, to the noninverting input 212 and inverting input 214 of a third differential amplifier 216. As before, this arrangement provides at the output 218 of the third amplifier 216 the second spatial derivative of voltage signals appearing on the inputs of the amplifiers 196 and 198. Thus, in the case of far-field signals whose second derivative at a local sensing site is essentially zero, such far-field signals will for all practical purposes not appear at the output 218 of the third amplifier immunizing the system from such interfering signals.

Figure 8:
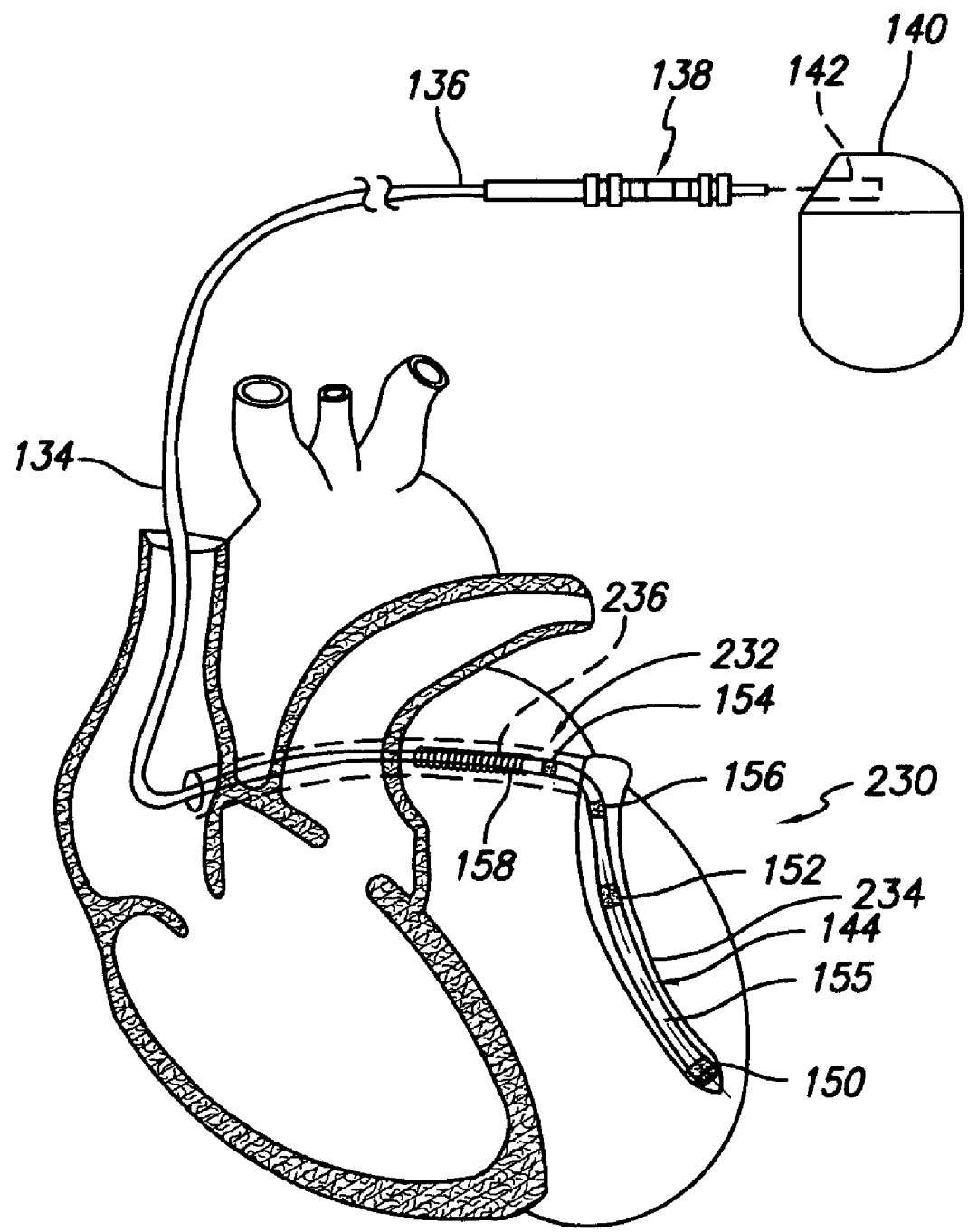
FIG. 8 is a perspective view of the anterior portion of a heart showing the distal end of the implantable lead of FIG. 5 placed within the coronary sinus region of the heart.

FIG. 8 is a perspective view of the anterior portion of a heart 230 showing portions of the relevant anatomy of the coronary sinus region 232. The lead body 134 is implanted in the coronary sinus region with the tip electrode 150 well within the farther reaches or distal extremity of the LPV vein 234 and the ring electrodes 152 and 156 within the proximal portion of the LPV vein. The ring electrode 154, in this particular, exemplary lead placement, resides in the distal end of the coronary sinus 236.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An implantable cardiac pacing and sensing system, the system being adapted to reject sensed far-field signals, the system comprising:
    a lead for transmitting electrical signals between an implantable medical device and selected body tissue in the heart, the lead comprising a lead body having a proximal end and a distal end, the proximal end of the lead body carrying a connector assembly connectable to the implantable medical device and the distal end of the lead body carrying a plurality of electrodes disposed in spaced-apart relationship along the distal end of the lead, the plurality of electrodes including a distal electrode, a proximal electrode and an intermediate electrode disposed between the distal and proximal electrodes; and an implantable medical device comprising a differential circuit having a plurality of inputs, the plurality of electrodes being electrically connected to respective inputs of said differential circuit, the differential circuit having an output providing a signal representing the difference between a first signal and a second signal, the first signal representing the difference between the magnitudes of the sensed signals generated by the distal and intermediate electrodes and the second signal representing the difference between the magnitudes of the sensed signals generated by the intermediate and proximal electrodes, the output signal being substantially devoid of far-field signals.

2. The system of claim 1 in which:

the intermediate electrode is positioned approximately midway between the distal and proximal electrodes.

3. The system of claim 1 in which:

the distal electrode comprises a tip electrode and the intermediate and proximal electrodes comprise ring electrodes.

4. The system of claim 1 in which:

the plurality of electrodes includes a tip electrode and each of the distal, intermediate and proximal electrodes comprises a ring electrode.

5. The system of claim 1 in which:

the differential circuit comprises a first, a second and a third differential amplifier;

the distal electrode is electrically connected to a first input of the first differential amplifier;

the proximal electrode is electrically connected to a first input of the second differential amplifier; and the intermediate electrode is electrically connected to a second input on each of the first and second differential amplifiers, the first and second differential amplifiers each having an output electrically connected as an input to the third differential amplifier, the third differential amplifier having an output providing a signal containing the second spatial derivative of a far-field signal incident upon the electrodes, said second spatial derivative being substantially zero.

6. A method of rejecting sensed far-field signals incident upon the electrodes of a cardiac pacemaker lead, said lead having a distal end carrying a plurality of spaced-apart electrodes including a distal electrode, a proximal electrode and an intermediate electrode positioned between the distal and the proximal electrodes, said electrodes generating signals including said far-field signals, the method comprising the steps of:

generating a first signal representing the difference between the magnitudes of the signals generated by the distal and intermediate electrodes;

generating a second signal representing the difference between the magnitudes of the signals generated by the intermediate and proximal electrodes; and generating a third signal representing the difference between the first and second signals, the third signal being substantially devoid of said far-field signals.

\* \* \* \* \*

UNITED STATES PATENT AND TRADEMARK OFFICE
CERTIFICATE OF CORRECTION

PATENT NO. : 7,587,239 B1  Page 1 of 1
APPLICATION NO. : 11/475482
DATED : September 8, 2009
INVENTOR(S) : Kroll et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 744 days.

Signed and Sealed this

Twenty-first Day of September, 2010

David J. Kappos
*Director of the United States Patent and Trademark Office*